US011232050B2

(12) United States Patent
Yamakita et al.

(10) Patent No.: US 11,232,050 B2
(45) Date of Patent: Jan. 25, 2022

(54) INFORMATION INTEGRATION APPARATUS

(71) Applicant: OPExPARK INC., Tokyo (JP)

(72) Inventors: Hiroshi Yamakita, Aichi (JP); Hideki Okuda, Aichi (JP)

(73) Assignee: OPExPARK INC., Tokyo (JP)

( * ) Notice: Subject to any disclaimer, the term of this patent is extended or adjusted under 35 U.S.C. 154(b) by 0 days.

(21) Appl. No.: 17/149,024

(22) Filed: Jan. 14, 2021

(65) Prior Publication Data

US 2021/0133126 A1 May 6, 2021

Related U.S. Application Data

(63) Continuation of application No. PCT/JP2019/027729, filed on Jul. 12, 2019.

(30) Foreign Application Priority Data

Jul. 17, 2018 (JP) ................................. 2018-134107

(51) Int. Cl.
*G06F 13/16* (2006.01)
(52) U.S. Cl.
CPC ................................. *G06F 13/1668* (2013.01)
(58) Field of Classification Search
None
See application file for complete search history.

(56) References Cited

U.S. PATENT DOCUMENTS

| 9,632,723 | B1* | 4/2017 | Gupta | G06F 3/0614 |
|---|---|---|---|---|
| 11,062,327 | B2* | 7/2021 | Biswas | G06Q 30/018 |
| 2007/0162634 | A1* | 7/2007 | Okazaki | G06F 13/387 |
| | | | | 710/15 |
| 2012/0173494 | A1* | 7/2012 | Friedlander | G06F 16/2457 |
| | | | | 707/687 |
| 2012/0331088 | A1* | 12/2012 | O'Hare | G06F 21/6227 |
| | | | | 709/214 |
| 2015/0278178 | A1 | 10/2015 | Okuda et al. | |

FOREIGN PATENT DOCUMENTS

| JP | 2015185125 A | 10/2015 |
|---|---|---|
| WO | 2015186631 A1 | 12/2015 |

OTHER PUBLICATIONS

International Search Report International Application No. PCT/JP2019/027729 dated Sep. 10, 2019.

(Continued)

*Primary Examiner* — Michael Sun
(74) *Attorney, Agent, or Firm* — Renner, Otto, Boisselle & Sklar, LLP

(57) ABSTRACT

An information integration apparatus includes providers, a middleware, and an application. The middleware executes processes of: assigning a reliability label to data supplied by a device to the provider, the reliability label corresponding to the provider; storing the data in a data storage device; reading the data from the data storage device, and supplying the read data to the application. The application provides, using the data, a display on a display device in a display mode corresponding to the reliability label assigned to the data.

9 Claims, 7 Drawing Sheets

(56) References Cited

OTHER PUBLICATIONS

Notification of Transmittal of Translation of the International Preliminary Report on Patentability Corresponding Application No. PCT/JP2019/027729 dated Jan. 29, 2021.
International Preliminary Report on Patentability Corresponding Application No. PCT/JP2019/027729 dated Jan. 19, 2021.
Written Opinion of the International Searching Authority Corresponding Application No. PCT/JP2019/027729 dated Sep. 10, 2019, English translation.

* cited by examiner

INFORMATION INTEGRATION APPARATUS

CROSS-REFERENCE TO RELATED APPLICATIONS

This application is a continuation application of PCT/JP2019/027729, which was filed on Jul. 12, 2019 and which claims the benefit of Japanese Patent Application No. 2018-134107 filed on Jul. 17, 2018 with the Japan Patent Office, and the entire disclosures of Japanese Patent Application No. 2018-134107 and PCT/JP2019/027729 are incorporated herein by reference.

TECHNICAL FIELD

The present disclosure relates to an information integration apparatus.

BACKGROUND ART

Patent Document 1 discloses an information integration apparatus. The information integration apparatus includes providers, a middleware, and applications. The providers each are connectable to a device.

PRIOR ART DOCUMENT

Patent Document

Patent Document 1: Japanese Unexamined Patent Application Publication No. 2015-185125

SUMMARY OF THE INVENTION

As a result of studies by the inventors, the following issues have been found. The information integration apparatus obtains and stores data from a device. The information integration apparatus provides a display on a display device and/or conducts control of an equipment using the stored data. However, the data, which the information integration apparatus obtains from the device, may include less reliable data. The information integration apparatus may provide an inaccurate display and/or may conduct inaccurate control with the less reliable data.

In one aspect of the present disclosure, it is preferable to provide an information integration apparatus capable of reducing adverse effects occurred when data obtained from a device is less reliable.

According to the one aspect of the present disclosure, there is provided an information integration apparatus comprising: providers each connectable to a device; a middleware; and at least one application. The information integration apparatus is connectable to a data storage device and a display device. The middleware is configured to execute processes of: assigning a reliability label to data supplied by the device to the provider, the reliability label corresponding to the provider supplied with the data; storing the data assigned with the reliability label in the data storage device; reading the data assigned with the reliability label from the data storage device; and supplying the read data to the application. The application is configured to provide, using the data supplied by the middleware, a display on the display device in a display mode corresponding to the reliability label assigned to the data.

The information integration apparatus according to the one aspect of the present disclosure assigns the reliability label to the data supplied by the device to the provider. The reliability label corresponds to the provider supplied with the data. The information integration apparatus according to the one aspect of the present disclosure provides the display on the display device. The mode for the display corresponds to the reliability label assigned to the data.

Thus, a user can see the display mode appeared on the display device and recognize the reliability of the data used for the display. As a result, for example, even if the information integration apparatus according to the one aspect of the present disclosure provides an inaccurate display using less reliable data, the user can recognize that contents of the display are less reliable.

According to another aspect of the present disclosure, there is provided an information integration apparatus comprising: providers each connectable to a device; a middleware; and at least one application. The information integration apparatus is connectable to a data storage device and a display device. The middleware is configured to execute processes of: assigning a reliability label to data supplied by the device to the provider, the reliability label corresponding to the provider supplied with the data; storing the data assigned with the reliability label in the data storage device; reading the data assigned with the reliability label from the data storage device; and supplying the read data to the application. The application is configured to control equipment, using the data supplied by the middleware. The application is configured to restrict control of the equipment based on the reliability label assigned to the data to be used for the control of the equipment.

The information integration apparatus according to the another aspect of the present disclosure assigns the reliability label to the data supplied by the device to the provider. The reliability label corresponds to the provider supplied with the data. The information integration apparatus according to the another aspect of the present disclosure restricts the control of the equipment based on the reliability label assigned to the data to be used for the control of the equipment.

Therefore, the information integration apparatus according to the another aspect of the present disclosure can be inhibited from conducting inaccurate control with the less reliable data.

MODES FOR CARRYING OUT THE INVENTION

Some example embodiments of the present disclosure will be described hereinafter by way of example with reference to the accompanying drawings.

First Embodiment

1. Configuration of Information Integration Apparatus 1

There will be described a configuration of an information integration apparatus 1 with reference to FIG. 1 to FIG. 3. The information integration apparatus 1 integrates, stores and displays various data in an operating room. The information integration apparatus 1 reads the stored data and controls equipment using the read data.

Figure 1:
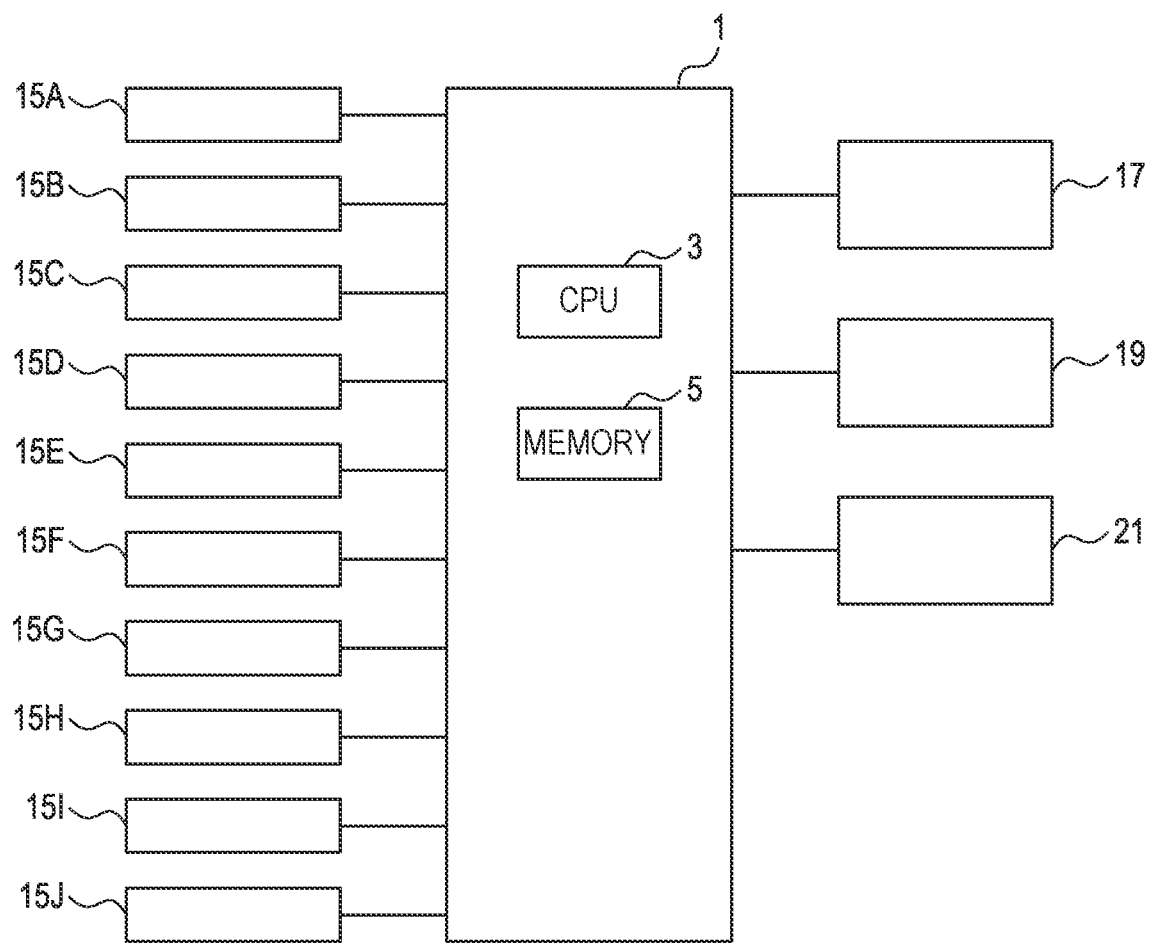
FIG. 1 is a block diagram showing a configuration of an information integration apparatus.

As shown in FIG. 1, the information integration apparatus 1 is a computer including a CPU 3 and a semiconductor memory such as a RAM or a ROM (hereinafter, referred to as "memory 5").

Functions of the information integration apparatus 1 are fulfilled by the CPU 3 executing programs stored in a non-transitory tangible storage medium. In this example, the memory 5 corresponds to the non-transitory tangible storage medium storing the programs. When a program is executed, a method corresponding to the program is performed. The information integration apparatus 1 may include one or more computers.

Figure 2:
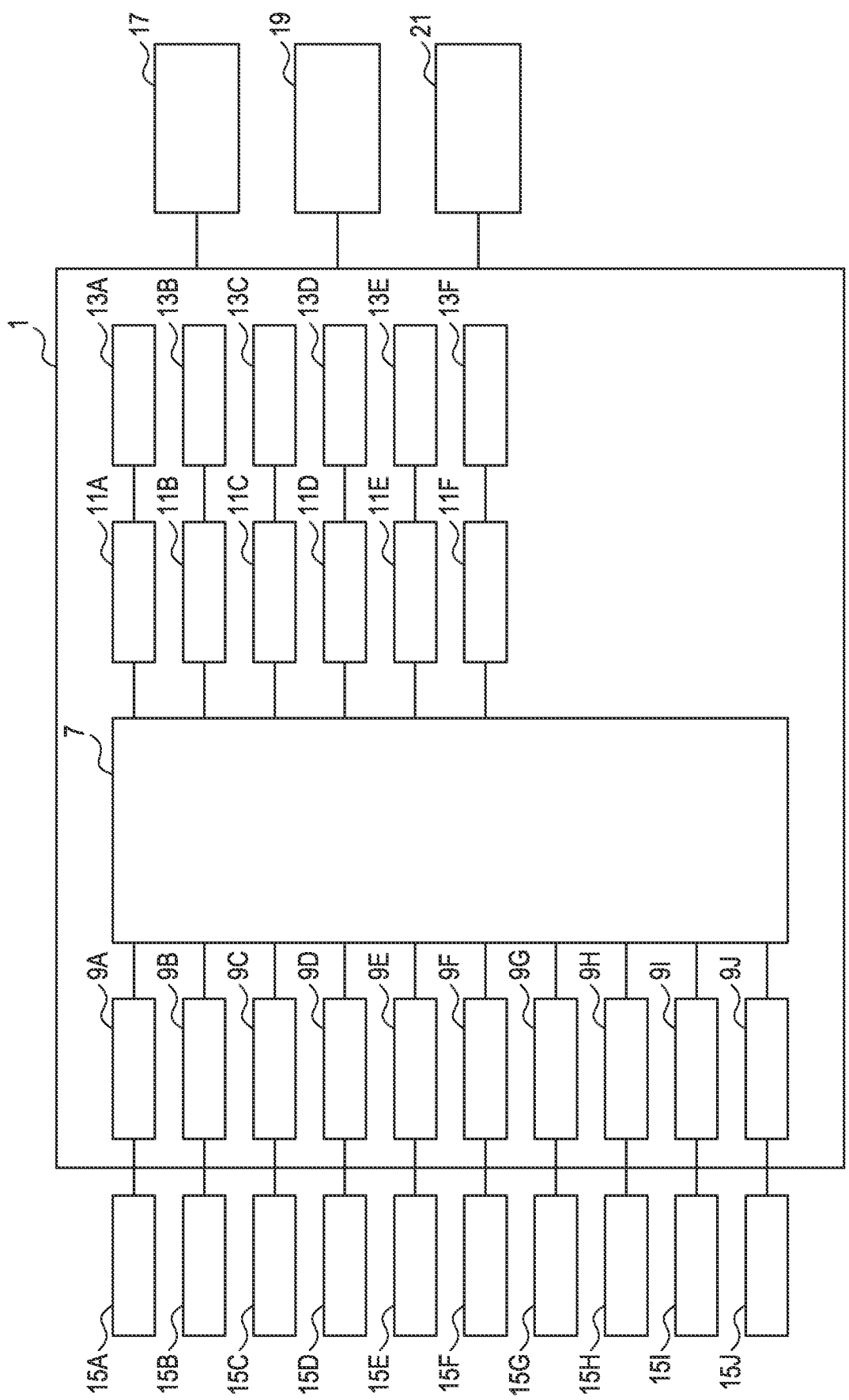
FIG. 2 is a block diagram showing a functional configuration of the information integration apparatus.

As shown in FIG. 2, the information integration apparatus 1 functionally includes a middleware 7, providers 9A to 9J, clients 11A to 11F, and applications 13A to 13F.

The provider 9A is coupled to the device 15A. Similarly, the providers 9B to 9J are each coupled to one of the devices 15B to 15J.

The devices 15A to 15J each generate data. The devices 15A to 15J each supply the data to the provider coupled thereto. The devices 15A to 15J are, for example, medical equipment and medical systems. Examples of the medical equipment may include biometric monitors, respiratory function monitors, circulatory dynamics monitors, sedation monitors, anesthesia machines, infusion pumps, syringes, blood purification apparatuses, artificial heart lung apparatuses, and circulation assisting apparatuses. Examples of the medical system may include IP cameras, medical gas systems, air conditioning systems, and isolation systems.

The middleware 7 is coupled to the providers 9A to 9J. The application 13A is coupled to the middleware 7 via the client 11A. Similarly, the applications 13B to 13F are each coupled to the middleware 7 via one of the clients 11B to 11F.

The application 13A controls a display device 19. The display device 19 displays an image. The applications 13B to 13F each control equipment coupled to the information integration apparatus 1, using data supplied by one or more of the devices 15A to 15J. Examples of the equipment to be controlled may include microscopes, anesthesia machines, syringe pumps, blood purification apparatuses, circulation assisting apparatuses, and medical systems.

The information integration apparatus 1 is coupled to a data storage device 17 and an input device 21. The data storage device 17 stores data. The input device 21 receives an input operation by a user. Examples of the user may include a doctor.

Figure 3:
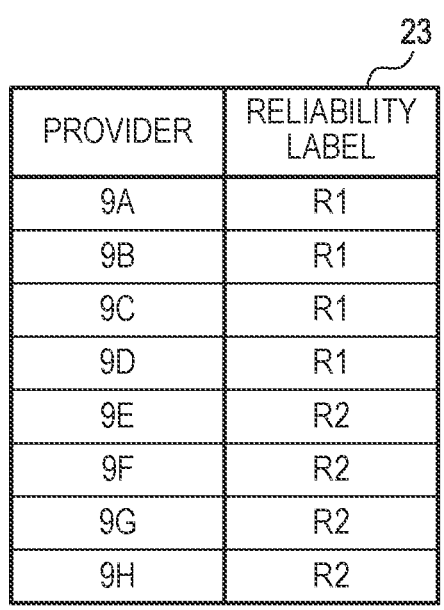
FIG. 3 is an explanatory diagram showing a configuration of a list.

The middleware 7 beforehand includes a list 23 shown in FIG. 3. In the list 23, the providers are each associated with a reliability label. The reliability label shows the reliability of the data. In the list 23, the reliability label includes two levels of R1 and R2. R1 is more reliable than R2.

2. Data Storage Process Executed by Information Integration Apparatus 1

Figure 4:
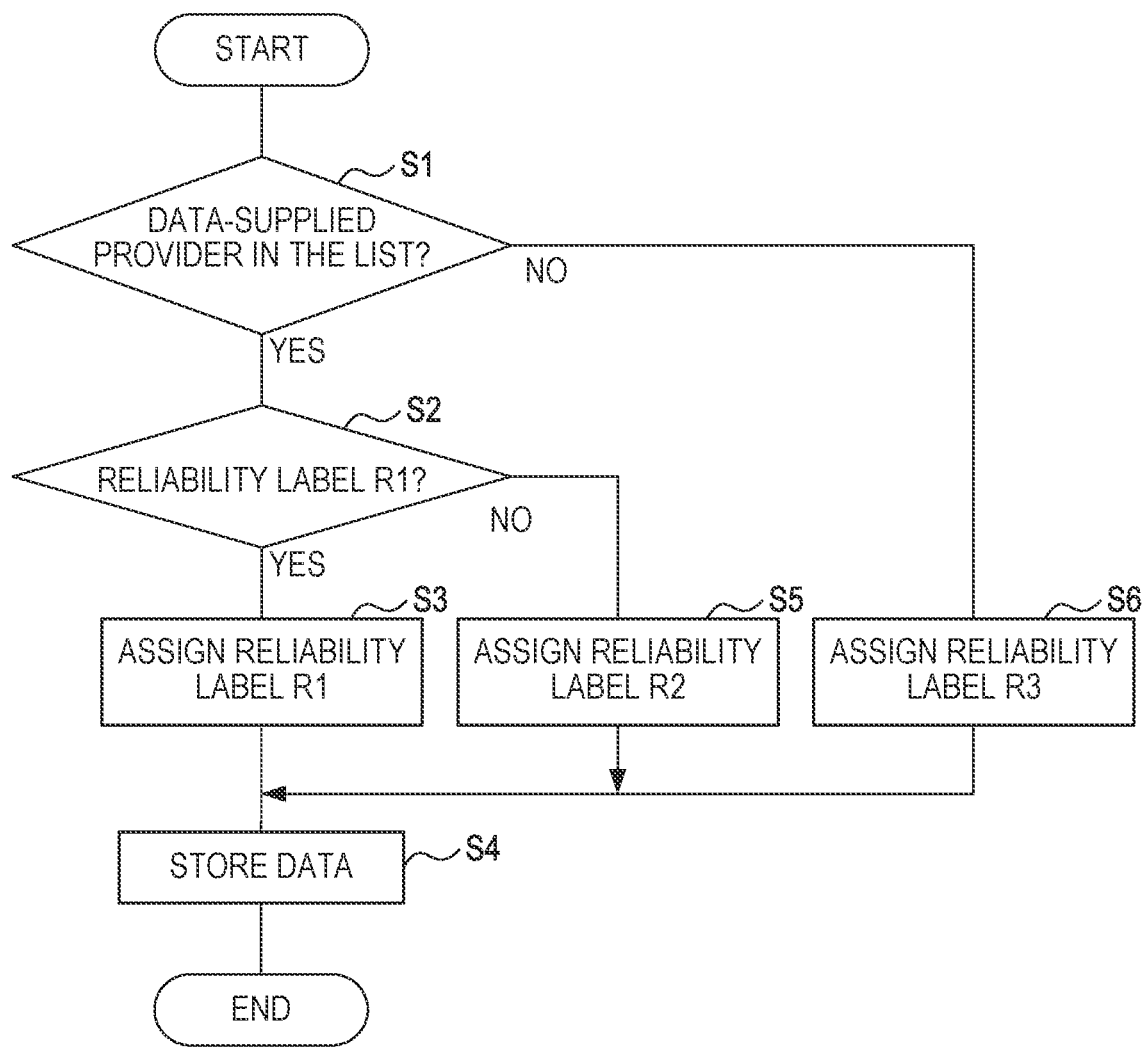
FIG. 4 is a flowchart showing a data storage process executed by the information integration apparatus.

The information integration apparatus 1 executes a data storage process when any one of the devices 15A to 15J supplies data to the information integration apparatus 1. The data storage process will be described with reference to FIG. 4. In S1 (Step 1), the middleware 7 firstly specifies a provider that is supplied with data (hereinafter, referred to as "data-supplied provider") among the providers 9A to 9J. Then, the middleware 7 determines whether the data-supplied provider is in the list 23.

For example, when the data-supplied provider is any one of the providers 9A to 9H, the data-supplied provider is in the list 23 as shown in FIG. 3. On the other hand, when the data-supplied provider is the provider 9I or 9J, the data-supplied provider is not in the list 23 as shown in FIG. 3.

When the data-supplied provider is in the list 23, the process proceeds to S2. When the data-supplied provider is not in the list 23, the process proceeds to S6.

In S2, the middleware 7 refers to the list 23 to determine whether the reliability label corresponding to the data-supplied provider is R1. For example, when the data-supplied provider is any one of the providers 9A to 9D, the reliability label corresponding to the data-supplied provider is R1 as shown in FIG. 3. On the other hand, when the data-supplied provider is any one of the providers 9E to 9H, the reliability label corresponding to the data-supplied provider is R2 as shown in FIG. 3.

When the reliability label corresponding to the data-supplied provider is R1, the process proceeds to S3. When the reliability label corresponding to the data-supplied provider is not R1, the process proceeds to S5.

In S3, the middleware 7 assigns a reliability label R1 to the supplied data.

In S4, the middleware 7 stores data, to which the reliability label is assigned in S3 or below-described S5 or S6, in the data storage device 17.

In S5, the middleware 7 assigns a reliability label R2 to the supplied data.

In S6, the middleware 7 assigns a reliability label R3 to the supplied data. The reliability label R3 indicates the reliability lower than the reliability label R2.

3. Display Process Executed by Information Integration Apparatus 1

There will be described a display process executed by the information integration apparatus 1 with reference to FIG. 5 and FIG. 6. The display process may be executed, for example, by a user's instruction. Alternatively, the display process may be executed, for example, upon request from the applications 13B to 13F.

Figure 5:
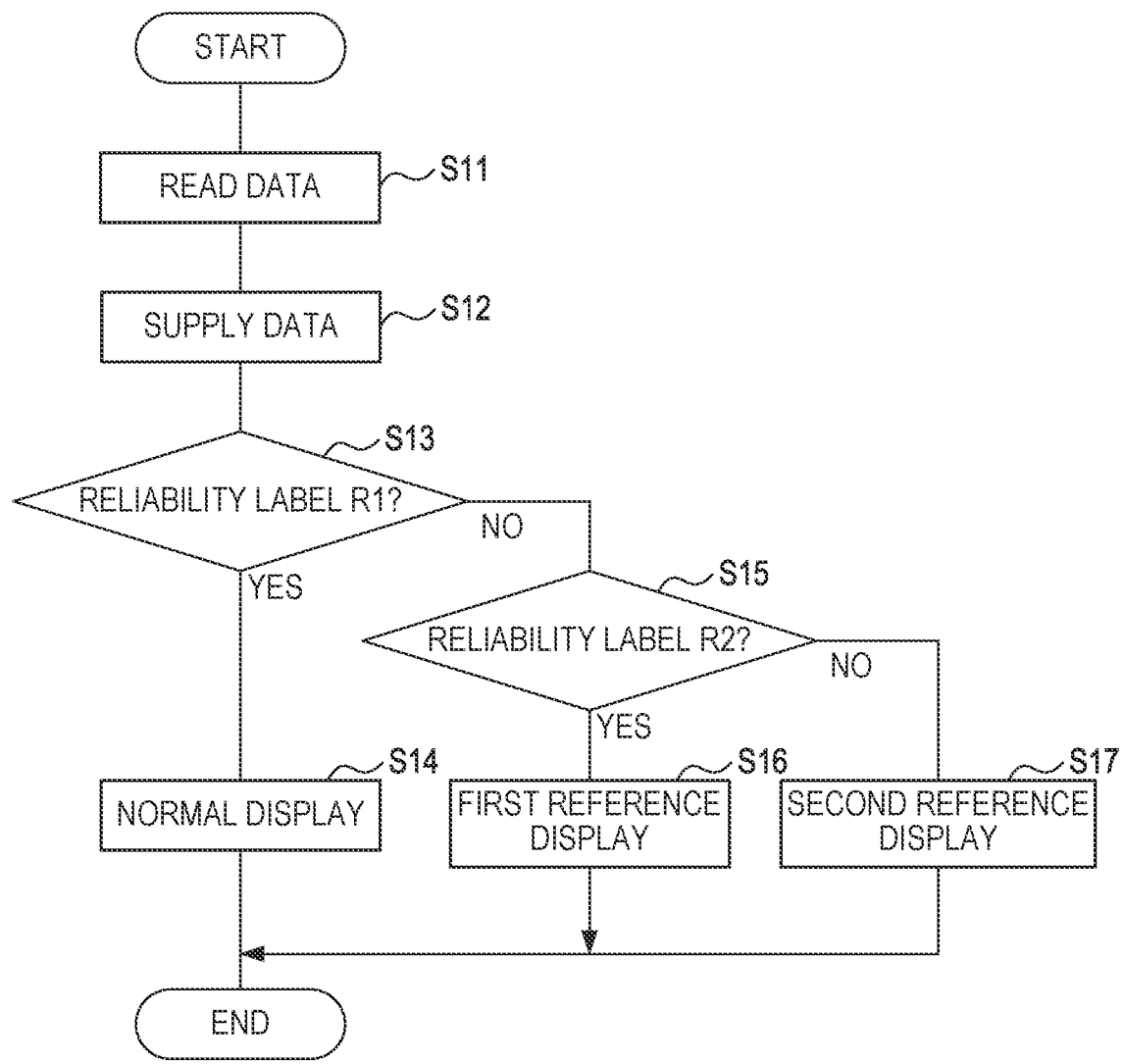
FIG. 5 is a flowchart showing a display process executed by the information integration apparatus.

In S11 of FIG. 5, the middleware 7 reads data from the data storage device 17. The data to be read is specified by the user or the applications 13B to 13F. The reliability label has been assigned to the read data.

In S12, the middleware 7 supplies the data, which is read in S11, to the application 13A.

In S13, the application 13A determines whether the reliability label, which is assigned to the supplied data supplied in S12, is R1. When the reliability label is R1, the process proceeds to S14. When the reliability label is not R1, the process proceeds to S15.

Figure 6A:
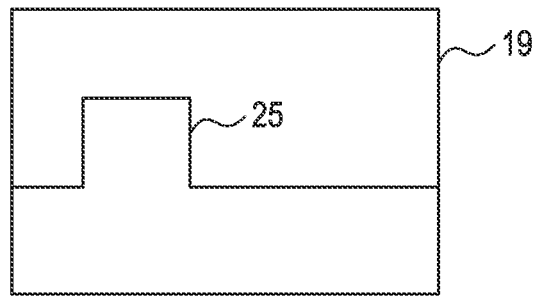
FIG. 6A is an explanatory diagram showing a normal display.

In S14, the application 13A provides a normal display on the display device 19 using the data supplied in S12. The normal display is a display in a mode in which, for example, data 25 is indicated by a solid line and a below-described frame 27 and an additional note indication 29 are not displayed as shown in FIG. 6A.

Examples of elements of the display mode may include a size, shape and color of a display, a width and type of a line indicating data, an existence/non-existence of flashing of the display, and an existence/non-existence of an additional indication.

In S15, the application 13A determines whether the reliability label assigned to the data, which is supplied in S12, is R2. When the reliability label is R2, the process proceeds to S16. When the reliability label is not R2, the process proceeds to S17. When the reliability label is not R2, the reliability label is R3.

Figure 6B:
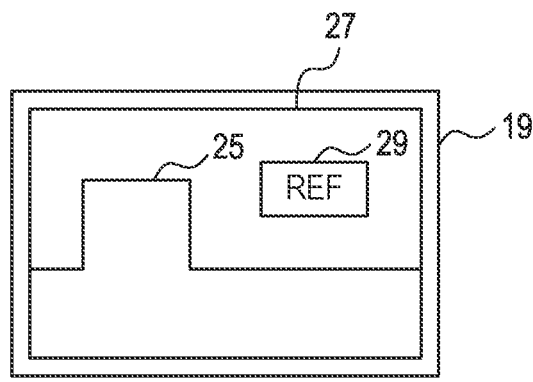
FIG. 6B is an explanatory diagram showing a first reference display.

In S16, the application 13A provides a first reference display on the display device 19 using the data supplied in S12. The first reference display is a display in a mode in which, for example and as shown in FIG. 6B, the data 25 is indicated by a solid line and the frame 27 and the additional note indication 29 are displayed. The frame 27 is a red frame. The frame 27 surrounds the data 25. The additional note indication 29 indicates a text of "REF" in a part of the display device 19. "REF" means that the data 25 is displayed for reference and that the data 25 is less reliable.

Figure 6C:
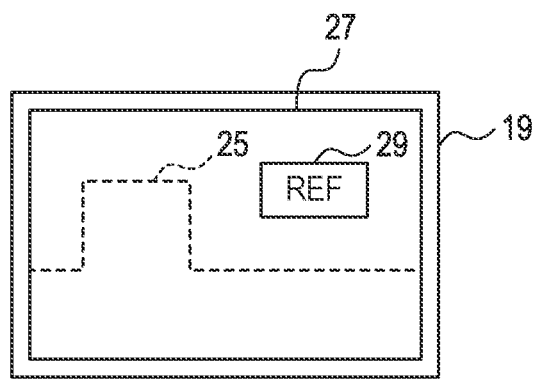
FIG. 6C is an explanatory diagram showing a second reference display.

In S17, the application 13A provides a second reference display on the display device 19 using the data supplied in S12. The second reference display is a display in a mode in which, for example and as shown in FIG. 6C, the data 25 is indicated by a dotted line, and the frame 27 and the additional note indication 29 are displayed. The frame 27 and the additional note indication 29 are the same as those described in S16.

4. Control Process Executed by Information Integration Apparatus 1

There will be described a control process executed by the information integration apparatus 1 with reference to FIG. 7. The control process is executed by, for example, by a user's instruction. Alternatively, the control process is executed, for example, upon request from the applications 13B to 13F.

Figure 7:
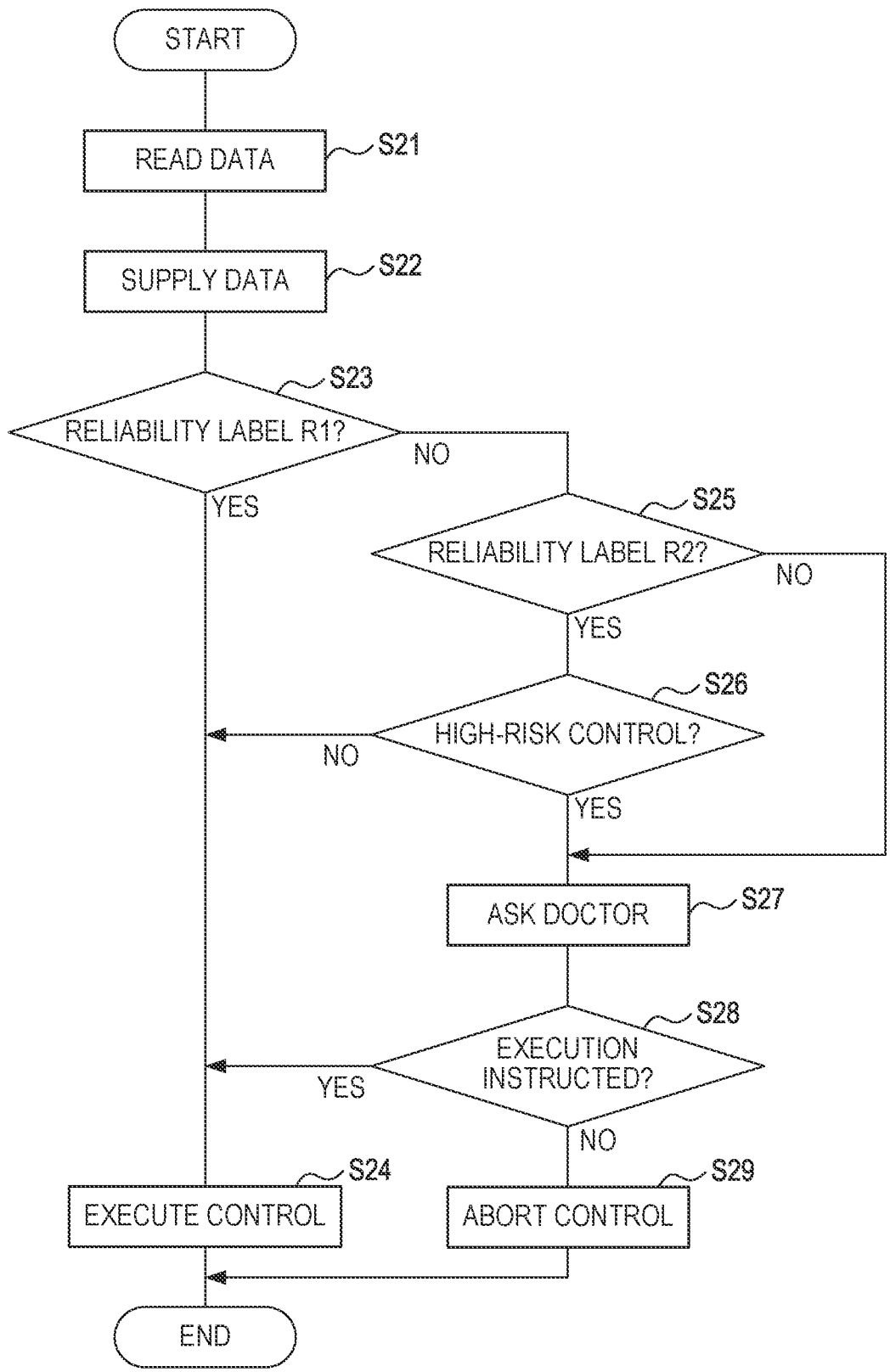
FIG. 7 is a flowchart showing a control process executed by the information integration apparatus.

In S21 of FIG. 7, the middleware 7 reads data from the data storage device 17. The data to be read is specified by a user or the applications 13B to 13F. The reliability label has been assigned to the read data.

In S22, the middleware 7 supplies the data, which is read in S21, to one or more applications 13B to 13F executing the control process (hereinafter, referred to as "execution application").

In S23, the execution application determines whether the reliability label assigned to the data, which is supplied in S22, is R1. When the reliability label is R1, the process proceeds to S24. When the reliability label is not R1, the process proceeds to S25.

In S24, the execution application controls equipment using the data supplied in S22.

In S25, the execution application determines whether the reliability label assigned to the data, which is supplied in S22, is R2. When the reliability label is R2, the process proceeds to S26. When the reliability label is not R2, the process proceeds to S27. When the reliability label is not R2, the reliability label is R3.

In S26, the execution application determines whether control to be executed by the execution application is control with a high risk (hereinafter, referred to as "high-risk control"). The information integration apparatus 1 beforehand includes a list of the high-risk control. The execution application refers to the list and determines whether the control to be executed is the high-risk control.

The high-risk control may be, for example, control having a high risk to a human body. Examples of the high-risk control may include, for example, control of an amount of anesthetic using blood pressure data. Examples of control that does not fall within the high-risk control may include control of changing zoom magnification of a microscope.

When the control to be executed by the execution application is the high-risk control, the process proceeds to S27. When the control is not the high-risk control, the process proceeds to S24.

In S27, the execution application provides a message of "Do you execute the control even if the data is less reliable?" on the display device 19. In response to this, a doctor can operate the input device 21 to instruct an execution of the control or abortion of the control.

In S28, the execution application determines whether the input device 21 has received an operation to instruct the execution of the control. The operation to instruct the execution of the control corresponds to an operation by a user. When the operation to instruct the execution of the control is received, the process proceeds to S24. When an operation to instruct the abortion of the control is received or no operation is received, the process proceeds to S29.

In S29, the execution application aborts the control. Abortion of the control corresponds to restricting the control.

5. Effects of Information Integration Apparatus 1

(1A) The middleware 7 assigns the data, which is supplied to the data-supplied provider, with the reliability label corresponding to the data-supplied provider. The reliability label indicates the reliability of the data.

The application 13A provides a display on the display device 19 using the data supplied by the middleware 7. The mode of the display corresponds to the reliability label assigned to the data. That is, the display mode varies depending on the reliability label assigned to the data. Thus, the user who sees the display mode on the display device 19 can recognize the reliability of the data used for the display. As a result, for example, even if the application 13A provides an inaccurate display using the less reliable data, the user can recognize that the contents of the display are not reliable.

(1B) The execution application restricts the control of the equipment based on the reliability label assigned to the data to be used for the control of the equipment. Thus, the execution application can be inhibited from executing inaccurate control using the less reliable data.

(1C) The execution application basically aborts the control when the reliability label assigned to the data is R2 and the control to be executed is the high-risk control. The execution application also basically aborts the control when the reliability label assigned to the data is R3. However, even in the above cases, the execution application executes the control when a doctor conducts the operation to instruct the execution of the control. That is, the execution application changes the restriction on the control in response to the operation by the doctor. Thus, the control can be executed on the doctor's responsibility.

(1D) The middleware 7 includes the list 23 in which the provider and the reliability label are associated with each other. The middleware 7 assigns the reliability label to the data using the list 23. This makes the process of assigning the reliability label easy. In addition, updating the list 23 makes it easy to change the correspondence relationship between the provider and the reliability label.

(1E) When the data is supplied to the provider, which is not included in the list 23, the middleware 7 assigns the data with the reliability label R3, which is different from the reliability label assigned when the data is supplied to the provider included in the list 23. This makes it easy to identify the data that is supplied to the provider, which is not included in the list 23.

Other Embodiments

Although an embodiment of the present disclosure has been described, the present disclosure is not limited to the above-described embodiment and may be modified in various forms.

(1) In the first embodiment, there are three types of reliability labels; however, there may be two, four, five, six, seven or more types of reliability labels.

In the case where two types of reliability labels are used, for example, the reliability labels of the providers in the list 23 may be all the same.

(2) The providers 9A to 9J each may have their own reliability label. When the data is supplied to the provider, the provider may assign the reliability label to the data.

(3) In S29, the execution application may execute the control within a limited range compared to the control executed in S24. Executing the control within the limited range corresponds to restricting the control of the equipment.

(4) When a negative determination is made in S23, the process may always proceed to S29.

(5) When a positive determination is made in S26, the process may always proceed to S29.

(6) When a negative determination is made in S25, the process may always proceed to S29.

(7) The display modes of the normal display, the first reference display, and the second reference display may take any form other than FIG. 6, and the display modes may be suitably set.

(8) Two or more functions achieved by one element in the aforementioned embodiment may be achieved by two or more elements. A function achieved by one element may be achieved by two or more elements. Two or more functions achieved by two or more elements may be achieved by one element. One function achieved by two or more elements may be achieved by one element. A part of the configuration of the aforementioned embodiment may be omitted. At least a part of the configuration of the aforementioned embodiment may be added to or replaced with the configuration of the aforementioned other embodiment. All embodiments included in the technological concept specified by the recitation of the claims are embodiments of the present disclosure.

(9) In addition to the above-described information integration apparatus, the present disclosure may be embodied in various forms, such as a system comprising the information integration apparatus as a component, a program to allow a computer to function as the information integration apparatus, a non-transitory tangible storage medium such as a semiconductor memory storing the program, a method of integrating information, a method of displaying data, and a method of controlling equipment.

The invention claimed is:

1. An information integration apparatus comprising:
providers each connectable to a device;
a middleware; and
at least one application, wherein
the information integration apparatus is connectable to a data storage device and a display device,
the middleware is configured to execute processes of:
assigning a reliability label to data supplied by the device to the provider, the reliability label corresponding to the provider supplied with the data;
storing the data assigned with the reliability label in the data storage device;
reading the data assigned with the reliability label from the data storage device; and
supplying the read data to the application, and
the application is configured to provide, using the data supplied by the middleware, a display on the display device in a display mode corresponding to the reliability label assigned to the data.

2. The information integration apparatus according to claim 1, wherein
the middleware is configured to include a list in which the provider and the reliability label are associated with each other, and
the middleware is configured to assign the reliability label to the data based on the list.

3. The information integration apparatus according to claim 2,
wherein when the data is supplied to the provider not included in the list, the middleware assigns the data with a reliability label different from the reliability level that is assigned when the data is supplied to the provider included in the list.

4. An information integration apparatus comprising:
providers each connectable to a device;
a middleware; and
at least one application, wherein
the information integration apparatus is connectable to a data storage device and a display device,
the middleware is configured to execute processes of:
assigning a reliability label to data supplied by the device to the provider, the reliability label corresponding to the provider supplied with the data;
storing the data assigned with the reliability label in the data storage device;
reading the data assigned with the reliability label from the data storage device; and
supplying the read data to the application,
the application is configured to control equipment, using the data supplied by the middleware, and
the application is configured to restrict control of the equipment based on the reliability label assigned to the data to be used for the control of the equipment.

5. The information integration apparatus according to claim 4, wherein
the middleware is configured to include a list in which the provider and the reliability label are associated with each other, and
the middleware is configured to assign the reliability label to the data based on the list.

6. The information integration apparatus according to claim 5, wherein when the data is supplied to the provider not included in the list, the middleware assigns the data with a reliability label different from the reliability level that is assigned when the data is supplied to the provider included in the list.

7. The information integration apparatus according to claim 4,
wherein the application is configured to change a restriction on the control of the equipment in accordance with an operation by a user.

8. The information integration apparatus according to claim 7, wherein
the middleware is configured to include a list in which the provider and the reliability label are associated with each other, and
the middleware is configured to assign the reliability label to the data based on the list.

9. The information integration apparatus according to claim 8,
wherein when the data is supplied to the provider not included in the list, the middleware assigns the data with a reliability label different from the reliability level that is assigned when the data is supplied to the provider included in the list.

* * * * *